United States Patent
Tanabe

(10) Patent No.: US 8,530,165 B2
(45) Date of Patent: Sep. 10, 2013

(54) NUCLEIC ACID DETECTION METHOD FOR DETERMINING IF ONE OR MORE ANALYTE NUCLEOTIDES ARE PRESENT IN A NUCLEIC ACID

(75) Inventor: Tetsuya Tanabe, Tokyo (JP)

(73) Assignee: Olympus Corporation, Tokyo (JP)

( * ) Notice: Subject to any disclaimer, the term of this patent is extended or adjusted under 35 U.S.C. 154(b) by 309 days.

(21) Appl. No.: 12/866,124

(22) PCT Filed: Jan. 29, 2009

(86) PCT No.: PCT/JP2009/051490
§ 371 (c)(1),
(2), (4) Date: Aug. 4, 2010

(87) PCT Pub. No.: WO2009/098998
PCT Pub. Date: Aug. 13, 2009

(65) Prior Publication Data
US 2010/0317019 A1    Dec. 16, 2010

(30) Foreign Application Priority Data

Feb. 5, 2008  (JP) ................................ P2008-025363

(51) Int. Cl.
*C12Q 1/68*    (2006.01)
*C12P 19/34*   (2006.01)

(52) U.S. Cl.
USPC ...................... 435/6.12; 435/91.1; 435/91.2

(58) Field of Classification Search
USPC ..................... 435/6.12, 91.1, 91.2
See application file for complete search history.

(56) References Cited

U.S. PATENT DOCUMENTS 5,863,736 A * 1/1999 Haaland ................ 435/6.16

FOREIGN PATENT DOCUMENTS

| JP | 2853864 | 3/1999 |
| JP | 2006-320217 | 11/2006 |
| WO | WO 01/34838 A1 | 5/2001 |
| WO | WO 01/42498 A1 | 6/2001 |
| WO | WO 2006/082685 A1 | 8/2006 |

(Continued)

OTHER PUBLICATIONS

Hwang, In-Taek et al., "Annealing control primer system for improving specificity of PCR amplification", BioTechniques (2003), vol. 35, No. 6, pp. 1180-1184.

(Continued)

*Primary Examiner* — Kenneth Horlick
(74) *Attorney, Agent, or Firm* — Scully, Scott, Murphy & Presser, P.C.

(57) ABSTRACT

The present invention is directed to a method with which one can detect a nucleic acid with sufficient accuracy, no matter the nucleotide length of a primer, and no matter if the analyte nucleotide consists of only a single nucleotide. Specifically disclosed is a method for detecting whether or not a nucleic acid sample contains a nucleic acid which has a target nucleotide sequence comprising one or more analyte nucleotide(s) in a nucleic acid sample. Firstly, in a step (a), a nucleic acid extension reaction is performed with use of a nucleic acid contained in the nucleic acid sample, an analyte nucleotide-identification primer, and a polymerase. Next, in a step (b), an extension product yielded from the step (a) is detected. The step (a) uses, as the primer, a polynucleotide which comprises a nucleotide sequence having an insertion site or a deletion site of one or more nucleotide(s), on the 5' side of nucleotide(s) corresponding to the analyte nucleotide(s), in a nucleotide sequence homologous or complementary to an analyte nucleotide-containing partial region of the target nucleotide sequence.

14 Claims, 4 Drawing Sheets

(56) References Cited

FOREIGN PATENT DOCUMENTS

| WO | 2007/022530 A2 | 2/2007 |
| WO | WO 2007/105673 A1 | 9/2007 |
| WO | 2007/130967 | * 11/2007 |

OTHER PUBLICATIONS

Chou, Lan-Szu et al., "Unlabeled oligonucleotide probes modified with locked nucleic acids for improved mismatch discrimination in genotyping by melting analysis", BioTechniques (2005), vol. 39, No. 5, pp. 644, 646, 648 and 650.

Abstract of Japanese Patent Publication No. 02-042999, dated Feb. 13, 1990.

International Search Report dated Feb. 24, 2009.

Notice of Reasons for Rejection dated Jun. 11, 2013 from corresponding Japanese Patent Application No. 2009-552451, together with an English language translation.

* cited by examiner

NUCLEIC ACID DETECTION METHOD FOR DETERMINING IF ONE OR MORE ANALYTE NUCLEOTIDES ARE PRESENT IN A NUCLEIC ACID

TECHNICAL FIELD

The present invention relates to a nucleic acid detection method for detecting whether or not a nucleic acid sample contains a nucleic acid which has a target nucleotide sequence comprising one or more analyte nucleotide(s), with higher accuracy, and a nucleic acid detection kit comprising a primer for use in the nucleic acid detection method.

DESCRIPTION OF THE RELATED ART

With the recent progress in genetic engineering technologies and gene recombination technologies, genetic tests through nucleic acid analyses have been widely used in the applications to medical services, researches, and industries. Such tests are to detect the presence of DNA which has a target nucleotide sequence within a sample, and have been applied not only to diagnosis and treatment of diseases, but also to food inspection and other various fields. In particular, a genetic polymorphism such as a SNP (Single Nucleotide Polymorphism) is considered to be a major factor contributing to the individual difference in the vulnerability against a specific disease such as cancer, the drug metabolizing capacity, and so forth. Genetic polymorphism analyses have been widely conducted not only in academic researches but also in actual clinical tests. Therefore, highly accurate and quick methods for detecting a genetic polymorphism have been enthusiastically developed.

As to the method for detecting a genetic polymorphism, there are many reported methods in which artificially synthesized polynucleotides such as probes and primers are used to examine the nucleotide sequences of nucleic acids. For example, some methods are to analyze the nucleotide sequence of a SNP serving as the subject to be analyzed and its neighboring region by molecular-biological enzymatic reactions. Such methods can be exemplified by: a method in which a region including a polymorphism such as a SNP is detected by PCR (Polymerase Chain Reaction) amplification; and a method in which a SNP is detected by a ligation reaction using a probe including the SNP to be detected at the 3' end and a probe including a nucleotide adjacent to the 5' side of the SNP, at the 5' end, and a subsequent determination regarding the obtainability of a polynucleotide bound with these two probes.

In particular, often employed SNP analysis methods are the SSP-PCR (Sequence Specific Primer-PCR) method and the ASP-PCR (Allele Specific Primer-PCR) method, in which a SNP is detected by PCR with use of a primer which is specifically bindable to a specific nucleotide sequence, allele, or the like, and a subsequent determination regarding the presence or absence of its PCR product (for example, refer to Patent Document 1). This is because that these methods are quite useful as the identification of a nucleotide sequence (genetic polymorphism) can be carried out concurrently with the enhancement of its signal, and thus the polymorphism detection by means of the SSP/ASP-PCR method is capable of a SNP detection even though only a few amount of specimens is available, or the nucleic acid concentration in a sample is very low, like a case of a specimen in a clinical test.

However, analysis methods by enzymatic reactions such as PCR latently involve a property to cause nonspecific reactions and are likely to bring a problem in terms of the analysis accuracy when analyzing only a single nucleotide difference within a nucleotide sequence, like a case for analyzing a SNP. In order to achieve high amplification efficiency while restraining such nonspecific nucleic acid amplifications, it is possible to take measures by individually performing a reaction per each primer at its optimum reaction condition. However, this method is not versatile because the reaction condition is different depending on each target nucleotide sequence to be detected. Therefore, tremendous time and effort are required for operations to detect a large number of specimens or to detect a plurality of SNP genotypes. Furthermore, in the case where a nucleic acid having the target nucleotide sequence forms a strong secondary structure, the nucleotide length of the primer tends to be elongated, whereas generally a long-chain primer involves a problem of having less ability to identify nucleotide(s).

In order to improve the SNP identification accuracy, various methods have been disclosed. For example, Patent Document 2 has disclosed a method in which a chromosome or its fragment including a specific nucleotide polymorphic site is subjected to the ASP-PCR method with use of a wild-type primer, one or two types of mutant primer(s), and a DNA polymerase, to thereby detect a nucleotide polymorphism based on the presence or absence of the primer extension. In this method, each primer has, at the second nucleotide from the 3' end, a nucleotide corresponding to each anticipated nucleotide of the nucleotide polymorphic site, with or without a substitution of at least one of the nucleotides between the 5' end and the third nucleotide from the 3' end, by nucleotide(s) which is (are) not complementary to the nucleotide(s) of the strand of the chromosome or its fragment to hybridize with the primer. This method is to improve the identification abilities of these primers by destabilizing a nearby region of the SNP to be detected. For example, a mismatch site is provided in a region to hybridize with a SNP-containing target nucleic acid to thereby make the hybridization between the wild-type primer and the wild-type allele more stable than the hybridization between the wild-type primer and a mutant allele, by which its identification ability can be improved.

Patent Document 1: Japanese Patent (Granted) Publication 2853864

Patent Document 2: PCT International Publication No. WO2001/042498 pamphlet

Patent Document 3: Japanese Unexamined Patent Application, First Publication No. 2006-320217

Patent Document 4: PCT International Publication No. WO2001/34838 pamphlet

DISCLOSURE OF INVENTION

In the method described in Patent Document 2, the identification accuracy for each polymorphism can be improved by introducing an appropriate mismatch corresponding to the respective SNP. However, this mismatch can be made by nucleotide substitution within a limited area of the primer, and thus the adjustable range is narrow. In addition, with use of such a modified primer, the success rate of the SNP detection will decrease, and it may not be possible to achieve a sufficient degree of identification accuracy depending on the type of the target nucleotide sequence to be detected. In particular, if the nucleotide length of the primer is long, problematically, it will not be possible, only by introducing a mismatch through nucleotide substitution, to achieve a sufficient degree of nucleotide identification ability.

It is an object of the present invention to provide a nucleic acid detection method which can detect a nucleic acid having a target nucleotide sequence with sufficient accuracy, when detecting with use of a primer to hybridize with the nucleic acid, no matter the nucleotide length of the primer, and no matter if the analyte nucleotide consists of only a single nucleotide.

In order to solve the above-mentioned problems, the inventors of the present invention have conducted intensive studies. As a result, they have discovered that, upon the detection of whether or not a nucleic acid sample contains a nucleic acid which has a target nucleotide sequence comprising one or more analyte nucleotide(s), it is possible to identify the nucleic acid having the nucleotide sequence, even by a single nucleotide difference, with sufficient accuracy, that is, highly accurate detection is possible even if the analyte nucleotide consists of only a single nucleotide, by employing a polynucleotide which comprises, on the 3' side, a nucleotide sequence homologous or complementary to an analyte nucleotide-containing partial region of the target nucleotide sequence as a primer, even though the nucleotide length of the primer is elongated by providing an insertion or deletion site of one or more nucleotide(s) on the 5' side of nucleotide(s) corresponding to the analyte nucleotide(s). This has led to the completion of the present invention.

That is, the present invention takes the following aspects.

(1) a nucleic acid detection method for detecting whether or not a nucleic acid sample contains a nucleic acid which has a target nucleotide sequence comprising one or more analyte nucleotide(s), the method comprising:

(a) performing a nucleic acid extension reaction with use of: the nucleic acid sample; an analyte nucleotide-identification primer being a polynucleotide which comprises a nucleotide sequence having an insertion site or a deletion site of one or more nucleotide(s), on the 5' side of the nucleotide(s) corresponding to said analyte nucleotide(s), in the nucleotide sequence homologous or complementary to a partial region containing said analyte nucleotide(s) of said target nucleotide sequence; and a polymerase; and (b) detecting an extension product yielded in (a).

(2) the nucleic acid detection method according to (1), wherein said insertion site or said deletion site of said analyte nucleotide-identification primer is located on the 5' side of the third nucleotide from the 3' end of the primer.

(3) the nucleic acid detection method according to (2), wherein said insertion site or said deletion site of said analyte nucleotide-identification primer is located on the 3' side of the twentieth nucleotide from the 3' end of the primer.

(4) the nucleic acid detection method according to any one of (1) to (3), wherein the method comprises, prior to (a),
(c) performing a nucleic acid extension reaction with use of: a nucleic acid in said nucleic acid sample; and an amplification primer being a polynucleotide which comprises a sequence complementary to said analyte nucleotide-identification primer, on the 5' end, and a nucleotide sequence homologous or complementary to a partial region of said target nucleotide sequence other than the partial region containing said analyte nucleotide(s), on the 3' end; so as to obtain a nucleic acid in which a nucleotide sequence homologous to the analyte nucleotide-identification primer is held on the 3' end of the target nucleotide sequence; and
in (a), a target nucleotide sequence-portion of the nucleic acid obtained in (c) is used as a template, and a 3' end-portion of the nucleic acid obtained in (c) as the analyte nucleotide-identification primer.

(5) the nucleic acid detection method according to any one of (1) to (4), wherein the insertion site is made by inserting one to three nucleotide(s).

(6) the nucleic acid detection method according to any one of (1) to (4), wherein the deletion site is made by deleting one to three nucleotide(s).

(7) the nucleic acid detection method according to any one of (1) to (6), wherein the nucleic acid extension reaction is a reaction to repeatedly perform a heat denaturation step, an annealing step, and an extension step.

(8) the nucleic acid detection method according to (7), wherein the annealing temperature in the annealing step and the extension reaction temperature in the extension step are the same.

(9) the nucleic acid detection method according to any one of (1) to (8), wherein the analyte nucleotide-identification primer is a polynucleotide having a length of 30 or more nucleotides.

(10) the nucleic acid detection method according to any one of (1) to (9), wherein the annealing temperature for between the analyte nucleotide-identification primer and the nucleic acid having the target nucleotide sequence, is 68° C. or higher.

(11) the nucleic acid detection method according to any one of (7) to (10), wherein the sum of the annealing time in the annealing step and the extension reaction time is three or more minutes.

(12) the nucleic acid detection method according to any one of (7) to (10), wherein the annealing time in the annealing step is elongated per each cycle.

(13) the nucleic acid detection method according to (12), wherein the annealing time in the final cycle is three or more minutes.

(14) the nucleic acid detection method according to any one of (1) to (6), wherein the polymerase is an enzyme having a strand displacement activity, and the nucleic acid extension reaction is a reaction to repeatedly perform an annealing step and an extension step in a fixed temperature condition.

(15) the nucleic acid detection kit for use in the nucleic acid detection method according to any one of (1) to (14), comprising the analyte nucleotide-identification primer.

(16) a nucleic acid detection kit according to (15), further comprising a polymerase and a reaction buffer solution.

With use of the nucleic acid detection method of the present invention, it is possible to identify a nucleic acid having a target nucleotide sequence, even by a single nucleotide difference, and even though the nucleotide length of the primer is long, with sufficient accuracy. Moreover, it is also possible to appropriately set the identification ability of the primer, by adjusting the position or the number of nucleotide(s) to be inserted or deleted, and thus much higher flexibility is given to the primer design as compared to the case where a mismatch is introduced by means of nucleotide substitution likewise of the method of Patent Document 2. For this reason, it becomes possible to more readily design an SNP-detectable primer having excellent nucleotide sequence identification ability, even for a kind of target nucleotide sequence for which it has been so far difficult for conventional methods to design a primer having high identification ability.

BRIEF DESCRIPTION OF THE REFERENCE SYMBOL

Figure 1A:
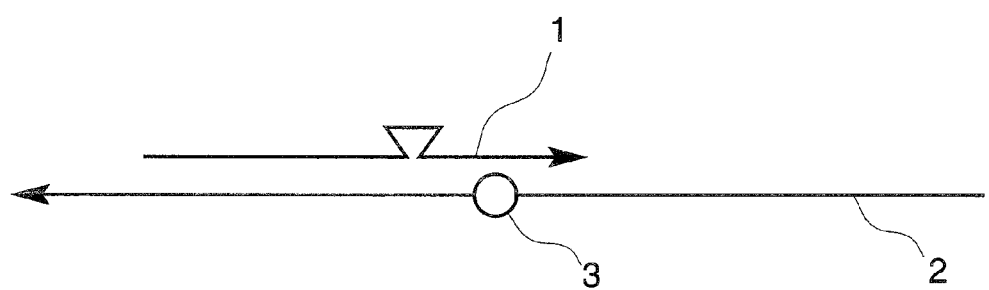
FIG. 1A is a schematic diagram showing a hybridization between a target nucleic acid and an analyte nucleotide-identification primer, wherein the analyte nucleotide-identification primer has a nucleotide insertion as an insertion site.

1. Analyte nucleotide-identification primer, 2. Target nucleic acid, 3. Analyte nucleotide

DETAILED DESCRIPTION OF THE PREFERRED EMBODIMENTS

The nucleic acid detection method of the present invention is a method for detecting whether or not a nucleic acid sample contains a nucleic acid which has a target nucleotide sequence comprising one or more analyte nucleotide(s), the method comprising:

(a) performing a nucleic acid extension reaction with use of: the nucleic acid sample; an analyte nucleotide-identification primer being a polynucleotide which comprises a nucleotide sequence having an insertion site or a deletion site of one or more nucleotide(s), on the 5' side of nucleotide(s) corresponding to the analyte nucleotide(s), in the nucleotide sequence homologous or complementary to a partial region containing the analyte nucleotide(s) of the target nucleotide sequence; and a polymerase; and (b) detecting an extension product yielded in (a).

In the present invention, the term "analyte nucleotide" refers to a nucleotide to be detected in a certain specific nucleotide sequence (target nucleotide sequence). Either a single analyte nucleotide or a plurality of analyte nucleotides may be employed. In addition, if a plurality of analyte nucleotides are employed, these analyte nucleotides may or may not be adjacent to each other. Moreover, in the design of the analyte-identification primer, it is necessary to arrange the analyte nucleotide(s) on the 3' side of the insertion or deletion site which has been introduced into the analyte nucleotide-identification primer.

The nucleic acid to be detected in the nucleic acid detection method of the present invention can be exemplified by a genetic polymorphism, a characteristic nucleotide of a disease genetic marker, and the like. The term "characteristic nucleotide of a genetic marker" means a nucleotide by which the difference between a nucleotide sequence having the genetic marker and a nucleotide sequence not having the genetic marker can be distinguished.

Here, the term "genetic polymorphism" is not specifically limited as long as the nucleotide sequence of a gene has a variation between individuals within a certain group of biological species. Examples of such a polymorphism can include a single nucleotide polymorphism (SNP), a microsatellite, an insertion, and a deletion. In the nucleic acid detection method of the present invention, SNP is particularly preferred as the genetic polymorphism included in the target nucleotide sequence. This is because that the nucleic acid detection method of the present invention is a method which enables highly accurate identification and detection of the difference between nucleotide sequences, even if it is an only single nucleotide difference, and the effect of the present invention to improve the nucleic acid identification ability can be more effectively exploited when applied to the SNP detection.

The target nucleotide sequence of the present invention is not specifically limited as long as it includes one or more analyte nucleotide(s) and its nucleotide sequence has been elucidated to a detectable degree by a gene recombination or like technique. Examples thereof may include nucleotide sequences existing in animal/plant chromosomes or bacterial/viral genes, and nucleotide sequences existing in biological RNAs such as mRNA. In particular, a nucleotide sequence of a region which includes a genetic polymorphism in a biological gene is preferred.

The nucleic acid sample of the present invention is not specifically limited as long as the sample can be expected to contain a nucleic acid which has the target nucleotide sequence (hereinunder, referred to as a target nucleic acid). The nucleic acid sample may be a biological sample collected from an animal or the like, a sample prepared from a cultured cell lysate or the like, and a nucleic acid solution extracted and purified from a biological sample or the like. In particular, human-derived biological samples to be used for clinical or other tests and nucleic acid solutions extracted and purified from such human-derived biological samples are preferred. In addition, the nucleic acid sample may be directly used after the collection from an organism, or may be prepared before use. The preparation method is not specifically limited as long as DNA, RNA, or such a nucleic acid contained in the biological sample is not impaired, and a usual preparation method for biological samples can be applied. Besides, DNA extracted and purified from a biological sample and amplified by PCR or like method, and cDNA synthesized from RNA contained in a biological sample with a reverse transcriptase may also be used.

The analyte nucleotide-identification primer for use in the nucleic acid detection method of the present invention is designed to be a polynucleotide which comprises a nucleotide sequence having an insertion or deletion site of one or more nucleotide(s), on the 5' side of nucleotide(s) corresponding to the analyte nucleotide(s), in a nucleotide sequence homologous or complementary to a partial region containing the analyte nucleotide(s) of the target nucleotide sequence. Accordingly, even if the analyte nucleotide consists of only a single nucleotide, it is possible to distinguish the target nucleic acid from non-target nucleic acids such as a nucleic acid which has an identical nucleotide sequence to that of the target nucleic acid except for the analyte nucleotide, with higher accuracy, and to specifically detect the target nucleic acid in the nucleic acid sample.

In the step (a), the nucleic acid extension reaction is performed with use of a nucleic acid in a nucleic acid sample as a template, and an analyte nucleotide-identification primer. The nucleotide length of the analyte nucleotide-identification primer is not specifically limited as long as the length allows the function as a primer in the nucleic acid extension reaction, and the length can be appropriately determined with consideration of the type of the target nucleotide sequence, the condition of the nucleic acid extension reaction, and the like. In the present invention, the nucleotide length of the analyte nucleotide-identification primer is preferably, for example, 30 or more nucleotides, but it may be more than 10 nucleotides and less than 30 nucleotides. A long nucleotide length of the primer causes a problem to impair the ability of the primer to identify the nucleotide sequence because the analyte nucleotide(s) accounts for less proportion in the entire region of the target nucleic acid to hybridize with the primer. However, with use of the nucleic acid detection method of the present invention, it becomes possible to design an analyte nucleotide-identification primer having high ability to identify the target nucleic acid, and to detect the target nucleic acid with high accuracy, even if the length of the region to hybridize with target nucleic acid is as long as 30 or more nucleotides.

In the present invention, the term "analyte nucleotide-identification primer" refers to a polynucleotide which comprises a nucleotide sequence having an insertion site or a deletion site made by insertion of deletion of one or more nucleotide(s), on the 5' side of nucleotide(s) corresponding to the analyte nucleotide(s), in a nucleotide sequence homologous or complementary to a partial region containing the analyte nucleotide(s) of the target nucleotide sequence (hereinunder, referred to as the analyte nucleotide recognition sequence). Here, the term "nucleotide(s) corresponding to the analyte nucleotide(s)" refers to nucleotide(s) homologous to the analyte nucleotide(s) if the analyte nucleotide-identification primer is a polynucleotide which comprises a nucleotide sequence homologous to the target nucleotide sequence, or refers to nucleotide(s) complementary to the analyte nucleotide(s) if the analyte nucleotide-identification primer is a polynucleotide which comprises a nucleotide sequence complementary to the target nucleotide sequence. Since the analyte nucleotide-identification primer of the present invention is a polynucleotide comprising the analyte nucleotide recognition sequence, the primer can specifically hybridize with the target nucleic acid or a nucleic acid being a complementary strand thereof, and can function as a starting point of the nucleic acid extension reaction.

The number of nucleotides to be inserted or deleted as an insertion site or a deletion site into or from the analyte nucleotide recognition sequence is not specifically limited as long as it is not less than one, and the number of nucleotides can be appropriately determined with consideration of the type of the analyte nucleotide recognition sequence, the type and the position of the nucleotide(s) to be inserted or deleted, the condition of the nucleic acid extension reaction in the step (a), and the like. A greater number of nucleotides to be inserted or deleted is more able to destabilize the hybridization between the analyte nucleotide-identification primer and the target nucleic acid. In the analyte nucleotide-identification primer of the present invention, particularly preferred insertion site or deletion site is a site made by insertion of one to three nucleotide(s) or a site made by deletion of one to three nucleotide(s).

The type of the nucleotide(s) to be inserted as an insertion site into the analyte nucleotide recognition sequence is not specifically limited as long as the inserted nucleotide(s) is (are) not hybridizable with the target nucleic acid. In addition, if two or more nucleotides are inserted, these nucleotides may be composed of either a plurality of a same type of nucleotides or a combination of different types of nucleotides. Preferred nucleotide to be inserted is adenine or thymine rather than guanine or cytosine.

The insertion site or the deletion site in the analyte nucleotide recognition sequence is not specifically limited as long as it is located on the 5' side of the nucleotide(s) corresponding to the analyte nucleotide(s). Accordingly, the insertion site or the deletion site can be appropriately determined by those skilled in the art with consideration of the type of the analyte nucleotide recognition sequence, the type and the position of the nucleotide(s) to be inserted etc., the condition of the nucleic acid extension reaction in the step (a) of the present invention, and the like. However, if the 3' end of the analyte nucleotide-identification primer becomes too unstable, it would be difficult, depending on the type of the target nucleotide sequence, to identify the target nucleotide sequence. For this reason, it is preferable that the insertion site or the deletion site is located on the 5' side of the third nucleotide from the 3' end of the analyte nucleotide-identification primer. In addition, similarly, it is also preferable that the insertion site or the deletion site is located on the 3' side of the twentieth nucleotide from the 3' end of the analyte nucleotide-identification primer, because the 3' end of the analyte nucleotide-identification primer can be more sufficiently destabilized by this arrangement.

Subsequently from the step (a), the detection method of the present invention performs the step (b), that is, the detection of an extension product yielded from the nucleic acid extension reaction which starts from the 3' end of the analyte nucleotide-identification primer by the hybridization of the analyte nucleotide-identification primer to the target nucleic acid in the nucleic acid sample, with use of the target nucleic acid as a template and with the aid of a polymerase. Then, the presence or absence of the analyte nucleotide is determined on the basis of the detection result. In order to determine whether or not the nucleic acid sample contains the target nucleic acid, it has been so far considered to be preferable that the analyte nucleotide(s) is (are) located in the vicinity of the 3' end of the analyte nucleotide-identification primer (for example, refer to Patent Document 1). On the other hand, in the nucleic acid detection method of the present invention, although it is preferable that the analyte nucleotide(s) is (are) located on the 3' end of the analyte nucleotide-identification primer, it is not always necessary to locate the analyte nucleotide(s) on the 3' end of the entire region of the primer as long as the analyte nucleotide(s) is (are) located on the 3' side of the insertion site or the deletion site. In this way, more choices are given to the position of the analyte nucleotide(s) in the analyte nucleotide-identification primer, and thus the primer can be more flexibly designed as compared to conventional methods.

The position of the analyte nucleotide(s) in the analyte nucleotide-identification primer is not specifically limited as long as the analyte nucleotide(s) is (are) located on the 3' side of the insertion site or the deletion site, and the position can be appropriately determined with consideration of the position of the insertion site or the deletion site, the number of nucleotides to be inserted or deleted, the target nucleotide sequence, and the like. In order to more effectively utilize the effect of the insertion site or the deletion site, the analyte nucleotide(s) is (are) preferably located in the vicinity of the insertion site or the deletion site.

The number of the insertion site(s) or the deletion site(s) in the analyte nucleotide recognition sequence may be either singular or plural. When a plurality of insertion sites or deletion sites are included, the analyte nucleotide should be located on the 3' side of the insertion site or the deletion site that resides on the most 3' side.

The degree of destabilization of the hybridization between the analyte nucleotide-identification primer and the target nucleic acid can be adjusted by appropriately selecting the position and the number of insertion site(s) or deletion site(s), the number and the type of nucleotide(s) to be inserted or deleted as the insertion site or the deletion site, the distance between the insertion site or the deletion site and the analyte nucleotide(s), and the like. In this way, because the primer design flexibility is high, the nucleic acid detection method of the present invention is capable of designing an analyte nucleotide-identification primer having high ability to identify the target nucleic acid, irrespective of the type of the target nucleotide sequence, the nucleotide length of the analyte nucleotide-identification primer, and the like.

Figure 1B:
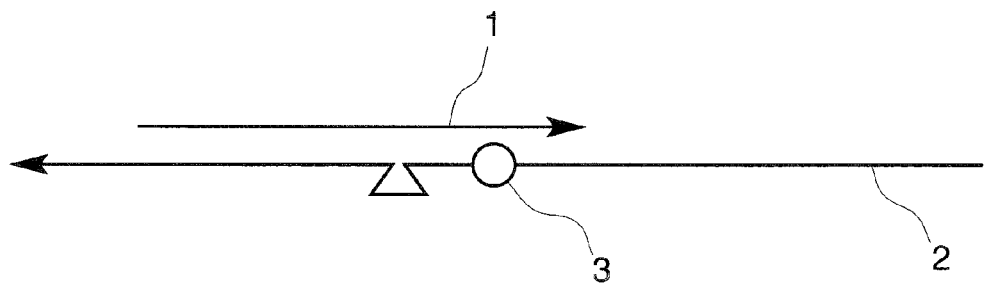
FIG. 1B is a schematic diagram showing a hybridization between the target nucleic acid and an analyte nucleotide-identification primer, wherein the analyte nucleotide-identification primer has a nucleotide deletion as a deletion site.

The reason why such high effect to identify the nucleic acid is given by the nucleic acid detection method of the present invention is not clear. However, it can be assumed to be such that: if a primer hybridizable to an analyte nucleotide-containing partial region of the target nucleic acid is employed as the analyte nucleotide-identification primer, it would be possible, by introducing the insertion site or the deletion site of one or more nucleotide(s) into the analyte nucleotide-identification primer, to destabilize the hybridization product between the analyte nucleotide-identification primer and the target nucleic acid, in the vicinity of the analyte nucleotide(s). FIG. 1A and FIG. 1B are schematic diagrams showing hybridizations between a target nucleic acid 2 having an analyte nucleotide 3 and an analyte nucleotide-identification primer 1. As shown in FIG. 1A, where a nucleotide is inserted as an insertion site, the hybridization product between the analyte nucleotide-identification primer 1 and the target nucleic acid 2 is destabilized by the insertion site consisting of the nucleotide which is not hybridizable with the target nucleic acid 2. On the other hand, as shown in FIG. 1B, where a nucleotide is deleted as a deletion site, the hybridization product between the analyte nucleotide-identification primer 1 and the target nucleic acid 2 is destabilized by the nucleotide of the target nucleic acid 2 which is complementary to the deleted nucleotide. As a result, the stability of the hybridization product between the analyte nucleotide-identification primer and the target nucleic acid would be increased sufficiently higher than the stability of the hybridization product between the analyte nucleotide-identification primer and a control nucleic acid (a nucleic acid which comprises a partial region differing from the target nucleotide sequence by at least a single nucleotide difference), making it possible to hybridize the analyte nucleotide-identification primer more specifically to the target nucleic acid. This can be assumed to contribute to the improvement of the ability of the analyte nucleotide-identification primer to identify the target nucleic acid.

If there are a plurality of target nucleic acids, and if the nucleic acid extension reaction in the step (a) of the nucleic acid detection method of the present invention is performed through PCR or like reaction whose optimum reaction condition varies in a primer-dependent manner, it is preferable to normalize the reaction condition of respective primers, including analyte nucleotide-identification primers and their counterpart primers, for use in the nucleic acid extension reaction. If the reaction condition of primers varies for each target nucleic acid, it is necessary to individually perform the step (a) per each target nucleic acid. However, it would be possible to collectively perform the step (a) under a same condition, by substantially equalizing (normalizing) the optimum reaction condition of primers to be used for all target nucleic acids. Therefore, a large number of target nucleic acids can be quickly and readily detected. The above-mentioned term "counterpart primer (with respect to an analyte nucleotide-identification primer)" refers to a primer to be used with the analyte nucleotide-identification primer as a primer set in the nucleic acid extension reaction. Specifically, if the nucleic acid extension reaction is PCR, and if the analyte nucleotide-identification primer is used as a forward primer, the counterpart primer will be a primer having a function as a reverse primer. In this case, either the analyte nucleotide-identification primer or the counterpart primer with respect to the analyte nucleotide-identification primer, may come to the 5' side of the target nucleotide sequence.

For example, when it comes to PCR, the reaction condition imposes a great influence on the annealing efficiency between the primer and the target nucleic acid serving as the template, and the reaction condition of the nucleic acid amplification can be normalized by substantially equalizing the annealing efficiencies of respective primers (for example, refer to Patent Document 3). Specifically, the annealing efficiencies, that is, the hybridization efficiencies can be substantially equalized to be 90% or higher, by designing the primers so that the region to hybridize with the target nucleic acid has a length of 30 or more nucleotides and the Tm value is 70 to 100° C., and by setting the reaction condition, particularly, by setting the sum of the annealing time and the extension reaction time to be three or more minutes. The nucleotide length of the region of the primer to hybridize with the target nucleic acid is preferably 30 to 60 nucleotides, more preferably 32 to 50 nucleotides, and particularly preferably 35 to 45 nucleotides.

The primer such as an analyte nucleotide-identification primer for use in the present invention can be designed in accordance with the target nucleotide sequence by a usual method. For example, it can be easily designed by using the nucleotide sequence information available from publicly known genome sequence data or SNP data with a general primer design tool. The publicly known genome sequence data is usually available on international nucleotide sequence databases, NCBI (National Center for Biotechnology Information), DDBJ (DNA Data Bank of Japan), and the like. In addition, the publicly known SNP data is available on databases such as a Japanese SNP database, JSNP (http://snp.ims.u-tokyo.ac.jp/index_ja.html) constructed by the Institute of Medical Science, the University of Tokyo. Examples of the primer design tool include Primer3 (Rozen, S., H. J. Skaletsky (1996), http://www-genome.wi.mit.edu/genome_software/other/primer3.html) and Visual OMP (DNA Software) which are available on the web.

The thus designed primer can be synthesized by any method well known in the art. For example, it may be synthesized by a custom oligo synthesis service or may be synthesized by the user him/herself using a commercially available synthesizer.

Moreover, each primer may have an additional sequence besides the region to hybridize with the target nucleic acid, to an extent that the amplification of the target nucleic acid is not inhibited. Examples of such an additional sequence include restriction enzyme recognition sequences and sequences for labeling a nucleic acid.

Furthermore, the analyte nucleotide-identification primer used in the nucleic acid detection method of the present invention may be labeled so as to facilitate the detection, analysis, and the like of the extension product yielded from the step (a). The labeling substance is not specifically limited as long as it can be used for labeling nucleic acids. Examples thereof include radioisotopes, fluorescent substances, chemiluminescent substances, and biotin.

The nucleic acid extension reaction in the step (a) utilizes the complementarity of nucleotides and is not specifically limited as long as it is a reaction to extend a nucleotide strand by having a nucleic acid as a template with the aid of a polymerase. It is possible to employ any one of various nucleic acid extension reactions usually performed in the field of genetic analysis and the like. The nucleic acid extension reaction can be exemplified not only by PCR and the NASBA (Nucleic Acid Sequence-Based Amplification) method, but also by the LAMP (Loop-Mediated Isothermal Amplification) method, the ICAN (Isothermal and Chimeric primer-initiated Amplification of Nucleic acids) method, Nicking endonuclease-mediated polymerase chain reaction, and other SDA (Strand Displacement Amplification) methods. In particular, the reaction preferably consists of repetitions of a heat denaturation step, an annealing step, and an extension step, likewise of PCR. The PCR may be real-time PCR, RT-PCR (Reverse Transcription-PCR), or multiplex PCR.

In addition, the polymerase for use in the step (a) is not specifically limited, and may be a usual polymerase for use in nucleic acid extension reactions. For example, either a DNA polymerase or an RNA polymerase may be used. Moreover, the polymerase may or may not be heat-resistant. Furthermore, the polymerase may have a proofreading function, and may have a strand displacement activity.

The reaction condition of the nucleic acid chain extension reaction in the step (a) is not specifically limited and can be appropriately determined with consideration of the type of the polymerase to be used, the Tm value of the primer, and the like. Similarly, the reagents such as nucleotides and reaction buffer solutions for use in the nucleic acid extension reaction are not specifically limited, and those for use in usual extension reactions can be used at usual amounts by considering the type of the nucleic acid extension reaction and the like.

In particular, regarding the step (a), if PCR is performed with a primer designed by the method disclosed in the Patent Document 3, as the analyte nucleotide-identification primer, it is preferable to set the annealing temperature approximately the same as the extension temperature. Usually, the Tm value of the primer increases as the nucleotide length gets longer. Therefore, the Tm value of the primer is often higher than the extension temperature if its length is 30 or more nucleotides. However, it is considered that, even if the extension temperature is significantly lower than the Tm value, the annealing efficiency can be improved irrespective of the type of the target nucleic acid, by conducting the annealing at about the extension temperature. In particular, it is preferable to conduct shuttle PCR in which the annealing and the extension reaction are carried out at the same time by setting the annealing temperature and the extension temperature the same. The extension temperature can be appropriately set with consideration of the heat resistance of the polymerase to be used, although preferred temperature is 68° C.

In addition, the amplification efficiency of the target nucleic acid can be improved, even if a long primer of 30 or more nucleotides is used, by setting the sum of the annealing time and the extension reaction time to be three or more minutes. The reason is assumed to be such that it would be possible to retain a sufficient time needing for accurate annealing and extension, even if a long primer is used, by elongating the sum of the annealing time and the extension reaction time. The sum of the annealing time and the extension reaction time is preferably from three to ten minutes, more preferably from five to ten minutes, yet more preferably from five to eight minutes, and particularly preferably about six minutes. Furthermore, as the extension time is long, it is possible to sufficiently amplify the target nucleic acid even if it has a long base pair length. Although PCR conducts repetitions of cycles, each consisting of a heat denaturation step, an annealing step, and an extension step, it is also preferable to elongate the annealing time per each cycle. By setting the annealing time short at the PCR initiation and elongating it as the number of cycles increases, it becomes possible to more effectively restrain nonspecific amplifications and to improve the reaction efficiency of the nucleic acid extension reaction; as a result of which, the total reaction time can be shortened. The annealing time may also be elongated stepwise per several cycles, rather than per each cycle. In addition, it is more preferable to set the annealing time in the final cycle to be three or more minutes.

Furthermore, in the step (b), if an extension product yielded from the nucleic acid extension reaction of the step (a) is detected, it can be determined, from this result, that the nucleic acid sample does contain the target nucleic acid. The method for detecting the extension product is not specifically limited, and the detection can be done with a usual detection method in the field of genetic analysis and the like, such as electrophoresis. For example, if the analyte nucleotide-identification primer is labeled with a labeling substance such as a fluorophore, the extension product can be detected by the indication from the labeling substance. Moreover, if real-time PCR is conducted as the nucleic acid extension reaction, the extension reaction and the detection of the yielded extension product can be performed at the same time. Otherwise, the extension product can also be detected by: previously adding a tag sequence to the 5' end of a primer for use in the nucleic acid extension reaction such as the analyte nucleotide-identification primer; conducting PCR with use of the nucleic acid in the reaction solution yielded from the nucleic acid extension reaction as a template and a polynucleotide comprising the tag sequence as a primer; and detecting the PCR product.

In addition, the target nucleic acid can also be detected in a similar manner by means of an SDA method (such as the LAMP method and the ICAN method) with use of a polymerase having a strand displacement activity, in which the nucleotide(s) corresponding to the analyte nucleotide(s) is (are) positioned on the 5' side of the nucleotide from which the polymerase starts the extension reaction, and furthermore the insertion or deletion site is provided in the 5' side of the nucleotide(s) corresponding to the analyte nucleotide(s). The LAMP method is a technique to amplify a nucleic acid while forming a dumbbell structure through strand displacement reactions. Repetitions of an annealing step and an extension step are performed under a fixed temperature condition at about 65° C., by which the reaction makes a continuous progress (for example, refer to Patent Document 4).

For example, in the nucleic acid detection method of the present invention, a step (c) is conducted so as to amplify the nucleic acid sample, prior to the step (a). In the step (c), an extension reaction is performed with use of a nucleic acid in the nucleic acid sample as a template and an amplification primer, so as to obtain a nucleic acid in which a nucleotide sequence homologous to the analyte nucleotide-identification primer is held on the 3' end of the target nucleotide sequence. Here, the term "amplification primer" refers to a polynucleotide which comprises a nucleotide sequence complementary to the analyte nucleotide-identification primer, on the 5' end, and a nucleotide sequence homologous or complementary to a partial region of the target nucleotide sequence other than the partial region containing the analyte nucleotide(s), on the 3' end. In addition, if the step (c) is conducted in advance, the subsequent step (a) will use a target nucleotide sequence-portion of the nucleic acid obtained from the step (c) as a template, a 3' end-portion of the nucleic acid obtained from the step (c) as the analyte nucleotide-identification primer. Here, the term "nucleotide sequence homologous to the analyte nucleotide-identification primer" means a nucleotide sequence having an insertion or deletion site of one or more nucleotide(s) on the 5' side of the nucleotide(s) corresponding to the analyte nucleotide(s) of the analyte nucleotide recognition sequence.

The nucleic acid obtained from the step (c) is a nucleic acid in which a sequence that can function as the analyte nucleotide-identification primer for the step (a) is located on the 3' end of target nucleotide sequence. That is, it is a nucleic acid having both a portion that can function as a template and a portion that can function as a primer for the nucleic acid extension reaction, within a molecular, as described in Patent Document 4. Hence, the step (a) can perform the nucleic acid extension reaction by having the target nucleotide sequence-portion of the nucleic acid obtained from the step (c) as a template, and the 3' end-portion of the nucleic acid obtained from the step (c) as the analyte nucleotide-identification primer.

Specifically speaking, since the analyte nucleotide-containing partial region of the target nucleotide sequence of the nucleic acid and the 3' end-portion of the same nucleic acid have complementary nucleotide sequences, this 3' end-portion is curved toward the 5' side due to their interaction and hybridization occurs therebetween; as a result of which, intramolecular loops are formed (dumbbell structure). Such a dumbbell structure can function in the same manner as that of the hybridization between template nucleic acid and primer. Therefore, an extension product can be obtained by a nucleic acid extension reaction with the aid of a polymerase.

In these methods, in the nucleic acid obtained from the extension reaction in the step (c), the region where the template target nucleic acid and the amplification primer hybridize with each other does not include the analyte nucleotide(s). Therefore, a nucleic acid which is different only by the difference in the analyte nucleotide(s) can also function as a template likewise of the target nucleic acid. However, the dumbbell structure of the nucleic acid obtained from the step (c) is dependent on the interaction between the analyte nucleotide-containing nucleotide sequence and the 3' end-portion functioning as the analyte nucleotide-identification primer. Thus, it would be difficult to form a dumbbell structure in the amplification product obtained with use of a nucleic acid having no analyte nucleotide(s) as a template, which makes it difficult to yield a nucleic acid extension product in the step (a).

In particular, in the present invention, the sequence identification ability of the analyte nucleotide-identification primer is improved by introducing the insertion or deletion site in the analyte nucleotide recognition sequence of the analyte nucleotide-identification primer. Therefore, the present invention is able to detect the target nucleic acid with much higher accuracy than conventional methods.

In addition, the analyte nucleotide-identification primer for use in the nucleic acid detection method of the present invention can be prepared as a kit. For example, an analyte nucleotide-identification primer for use in the detection of a target nucleic acid and its counterpart primer can be prepared in a nucleic acid detection kit. In addition, a plurality of types of analyte nucleotide-identification primers and the like may also be prepared in a nucleic acid detection kit. These nucleic acid detection kits preferably include a polymerase, nucleotides, reaction buffer solutions, and such reagents, for use in the nucleic acid chain extension reaction. The use of such a kit will enable quick and convenient detection of the target nucleic acid.

Next is a more detailed description of the present invention with reference to examples. However, the present invention is not to be considered as being limited by the following examples.

EXAMPLE 1

The 131st, 686th, 608th to 131st, 687th, and 270th nucleotides of human chromosome 5 were employed as the target nucleotide sequences. Primers having insertion or deletion sites were constructed based on known primers which had been confirmed to be able to amplify these regions, and the detection of the target nucleic acid was attempted by using the thus constructed primers.

Primer Design

Using a primer set consisting of a forward primer (Fw) and a reverse primer (Re) which had been previously confirmed to be able to amplify the regions of the 131st, 686th, 608th to 131st, 687th, and 270th nucleotides of human chromosome 5, primers were designed so that one to three nucleotide(s) was (were) inserted in some point between the first to the eighth nucleotide from the 3' end of Fw. The respective sequences of the thus designed primers are shown in Table 1. Regarding the insertion of nucleotide(s), the type of the nucleotide(s) to be inserted was determined so that the region to hybridize with the target nucleic acid would not be shifted by the inserted nucleotide(s). Table 2 shows the relationship between the types of two consecutive nucleotides (nucleotide on the 5' side and nucleotide on the 3' side) and the type of a nucleotide inserted therebetween.

TABLE 1

| Name | Seq |
|---|---|
| Fw | AGGTGTCAGACATACCCTCTTTTTGGAGATTTCCTGTTCC |
| Re | AATTGCTCTGCTCTTGTAAGTCTGGGATGCTTTCCT |
| Fw_I01_P01 | AGGTGTCAGACATACCCTCTTTTTGGAGATTTCCTGTTCTC |
| Fw_I01_P02 | AGGTGTCAGACATACCCTCTTTTTGGAGATTTCGTGTTACC |
| Fw_I01_P03 | AGGTGTCAGACATACCCTCTTTTTGGAGATTTCCTGTATCC |
| Fw_I01_P04 | AGGTGTCAGACATACCCTCTTTTTGGAGATTTGCTGATTCC |
| Fw_I01_P05 | AGGTGTCAGACATACCCTCTTTTTGGAGATTTCCTAGTTCC |
| Fw_I01_P06 | AGGTGTCAGACATACCCTCTTTTTGGAGATTTCCATGTTCC |
| Fw_I01_P07 | AGGTGTCAGACATACCCTCTTTTTGGAGATTCTCTGTTCC |
| Fw_I01_P08 | AGGTGTCAGACATACCCTCTTTTTGGAGATTTACCTGTTCC |
| Fw_I02_P02 | AGGTGTCAGACATACCCTCTTTTTGGAGATTTCCTGTTAACC |
| Fw_I02_P03 | AGGTGTCAGACATACCCTCTTTTTGGAGATTTCCTGTAATCC |
| Fw_I02_P04 | AGGTGTCAGACATACCCTCTTTTTGGAGATTTCCTGAATTCC |
| Fw_I02_P05 | AGGTGTCAGACATACCCTCTTTTTGGAGATTTCCTAAGTTCC |
| Fw_I02_P06 | AGGTGTCAGACATACCCTCTTTTTGGAGATTTCCAATGTTCC |
| Fw_I02_P07 | AGGTGTCAGACATACCCTCTTTTTGGAGATTTCTTCTGTTCC |
| Fw_I03_P03 | AGGTGTCAGACATACCCTCTTTTTGGAGATTTCCTGTAAATCC |
| Fw_I03_P04 | AGGTGTCAGACATACCCTCTTTTTGGAGATTTCCTGAAATTCC |
| Fw_I03_P05 | AGGTGTCAGACATACGCTCTTTTTGGAGATTTCCTAAAGTTCC |

TABLE 1-continued

| Name | Seq |
|---|---|
| Fw_I03_P06 | AGGTGTCAGACATACCCTCTTTTTGGAGATTTCCAAATGTTCC |
| Fw_I03_P07 | AGGTGTCAGACATACCCTCTTTTTGGAGATTTCTTTCTGTTCC |
| Fw_I03_P08 | AGGTGTGAGACATACCCTCTTITTGGAGATTTAAACGTGTTCC |

TABLE 2

| 5' Side Nucleotide | 3' Side Nucleotide | Inserted Nucleotide |
|---|---|---|
| A | A | T |
| A | T | C |
| A | G | T |
| A | C | T |
| T | A | C |
| T | T | A |
| T | G | A |
| T | C | A |
| G | A | T |
| G | T | A |
| G | G | T |
| G | C | T |
| C | A | T |
| C | T | A |
| C | G | T |
| C | C | T |

Nucleic Acid Extension Reaction and Detection of Extension Product

PCR was conducted with use of the thus designed respective primers as of Table 1 as the forward primers, and their PCR products were detected. Re was used as the reverse primer in all cases. In addition, the Human Genome Mix (manufactured by NovaGene) was used as the template.

Specifically speaking, 5 µL of 2×QIAGEN Multiplex PCR Master Mix (manufactured by QIAGEN) was added with 5 ng of the Genome Mix, and the forward primer and the reverse primer respectively at the final concentrations of 100 nM, to thereby prepare 10 µL of a reaction solution. The reaction solution was subjected to PCR through a treatment at 95° C. for 15 seconds, and subsequent 30 thermal cycles of 95° C. for 30 seconds and 68° C. for 6 minutes. Thereafter, 1 µL was each collected from the yielded reaction solution, and was detected for the PCR product by electrophoresis. The detection results are shown in Table 3. In the table, the term "Insertion position" represents the position at which nucleotide(s) was (were) inserted in the forward primer used in the PCR (the positional order of nucleotide counted from the 3' end of Fw to the 5' side, at which nucleotide(s) was (were) inserted), and the term "Number of inserted nucleotide(s)" represents the number of nucleotide(s) inserted in the forward primer used in the PCR. The "A" represents a result in which a sufficient amount of PCR product was detected (Excellent), the "B" represents a result in which a very small amount of PCR product was detected (Fair), and the "C" represents a result in which no PCR product was detected (Poor).

TABLE 3

| Number of Inserted Nucleotides | Insertion Position | | | | | | | |
|---|---|---|---|---|---|---|---|---|
| | 1 | 2 | 3 | 4 | 5 | 6 | 7 | 8 |
| 1 | C | C | B | A | A | A | A | A |
| 2 | — | C | C | C | B | A | A | — |
| 3 | — | — | C | C | C | B | A | A |

A: Excellent
B: Fair
C: Poor

It was continued that, when nucleotide(s) was (were) artificially inserted into the primer, the PCR amplification was suppressed depending on the insertion position and the number of inserted nucleotide(s). Specifically speaking, it was found that the PCR amplification was more suppressed as the insertion position of nucleotide(s) got closer to the 3' end, and that the PCR amplification was even more suppressed as the number of inserted nucleotide(s) increased if the insertion position was the same. From these results, apparently, it is possible to adjust the degree of the destabilization of the hybridization between the primer and the target nucleic acid by adjusting the insertion position and the number of inserted nucleotide(s).

EXAMPLE 2

It was examined whether or not a primer having a nucleotide insertion site was able to distinguish a single nucleotide difference, with use of the Fw_I01_P04 (primer in which one nucleotide was inserted on the 5' side of the fourth nucleotide from the 3' end of Fw) and the Fw_I02_P06 (primer in which two nucleotides were inserted on the 5' side of the sixth nucleotide from the 3' end of Fw), which were confirmed to be able to amplify the PCR product in the example 1, and the forward primer (Fw) as a control.

Primer Design

First, primers were designed by using the Fw_I01_P04 and the Fw_I02_P06 so that a nucleotide on the 3' side of respective insertion position was substituted with another nucleotide. The respective sequences of the thus designed primers are shown in Table 4.

TABLE 4

| Name | Seq | No |
|---|---|---|
| Fw | AGGTGTCAGACATACCCTCTTTTTGGAGATTTCCTGTTCC | 1 |
| Fw_I01_P04 | AGGTGTCAGACATACCCTCTTTTTGGAGATTTCCTGATTCC | 2 |
| Fw_I02_P06 | AGGTGTCAGACATACCCTCTTTTTGGAGATTTCCAATGTTCC | 3 |
| Fw_1A | AGGTGTCAGACATACCCTCTTTTTGGAGATTTCCTGTTCA | 4 |
| Fw_1T | AGGTGTCAGACATACCCTCTTTTTGGAGATTTCCTGTTCT | 5 |
| Fw_1G | AGGTGTCAGACATACCCTCTTTTTGGAGATTTCCTGTTCG | 6 |
| Fw_I01_P04_1A | AGGTGTCAGACATACCCTCTTTTTGGAGATTTCCTGATTCA | 7 |
| Fw_I01_P04_1T | AGGTGTCAGACATACCCTCTTTTTGGAGATTTCCTGATTCT | 8 |

TABLE 4-continued

| Name | Seq | No |
|---|---|---|
| Fw_I01_P04_1G | AGGTGTCAGACATACCCTCTTTTTGGAGATTTCCTGATTCG | 9 |
| Fw_I01_P04_2A | AGGTGTCAGACATACCCTCTTTTTGGAGATTTCCTGATTAC | 10 |
| Fw_I01_P04_2T | AGGTGTCAGACATACCCTCTTTTTGGAGATTTCCTGATTTC | 11 |
| Fw_I01_P04_2G | AGGTGTCAGACATACCCTCTTTTTGGAGATTTCCTGATTGC | 12 |
| Fw_I01_P04_3A | AGGTGTCAGACATACCCTCTTTTTGGAGATTTCCTGATACC | 13 |
| Fw_I01_P04_3C | AGGTGTCAGACATACCCTCTTTTTGGAGATTTCCTGATCCC | 14 |
| Fw_I01_P04_3G | AGGTGTCAGACATACCCTCTTTTTGGAGATTTCCTGATGCC | 15 |
| Fw_I01_P04_4A | AGGTGTCAGACATACCCTCTTTTTGGAGATTTCCTGAATCC | 16 |
| Fw_I01_P04_4C | AGGTGTCAGACATACCCTCTTTTTGGAGATTTCCTGACTCC | 17 |
| Fw_I01_P04_4G | AGGTGTCAGACATACCCTCTTTTTGGAGATTTCCTGAGTCC | 18 |
| Fw_I01_P06_1A | AGGTGTCAGACATACCCTCTTTTTGGAGATTTCCAATGTTCA | 19 |
| Fw_I02_P06_1T | AGGTGTCAGACATACCCTCTTTTTGGAGATTTCCAATGTTCT | 20 |
| Fw_I02_P06_1G | AGGTGTCAGACATACCCTCTTTTTGGAGATTTCCAATGTTCG | 21 |
| Fw_I02_P06_2A | AGGTGTCAGACATACCCTCTTTTTGGAGATTTCCAATGTTAC | 22 |
| Fw_I02_P06_2T | AGGTGTCAGACATACCCTCTTTTTGGAGATTTCCAATGTTTC | 23 |
| Fw_I02_P06_2G | AGGTGTCAGACATACCCTCTTTTTGGAGATTTCCAATGTTGC | 24 |
| Fw_I02_P06_3A | AGGTGTCAGACATACCCTCTTTTTGGAGATTTCCAATGTACC | 25 |
| Fw_I02_P06_3C | AGGTGTCAGACATACCCTCTTTTTGGAGATTTCCAATGTCCC | 26 |
| Fw_I02_P06_3G | AGGTGTCAGACATACCCTCTTTTTGGAGATTTCCAATGTGCC | 27 |
| Fw_I02_P06_4A | AGGTGTCAGACATACCCTCTTTTTGGAGATTTCCAATGATCC | 28 |
| Fw_I02_P06_4C | AGGTGTCAGACATACCCTCTTTTTGGAGATTTCCAATGCTCC | 29 |
| Fw_I02_P06_4G | AGGTGTCAGACATACCCTCTTTTTGGAGATTTCCAATGGTCC | 30 |
| Fw_I02_P06_5A | AGGTGTCAGACATACCCTCTTTTTGGAGATTTCCAATATTCC | 31 |
| Fw_I02_P06_5T | AGGTGTCAGACATACCCTCTTTTTGGAGATTTCCAATTTTCC | 32 |
| Fw_I02_P06_5C | AGGTGTCAGACATACCCTCTTTTTGGAGATTTCCAATCTTCC | 33 |
| Fw_I02_P06_6A | AGGTGTCAGACATACCCTCTTTTTGGAGATTTCCAAAGTTCC | 34 |
| Fw_I02_P06_6C | AGGTGTCAGACATACCCTCTTTTTGGAGATTTCCAACGTTCC | 35 |
| Fw_I02_P06_6G | AGGTGTCAGACATACCCTCTTTTTGGAGATTTCCAAGGTTCC | 36 |

Nucleic Acid Extension Reaction and Detection of Extension Product

Figure 2:
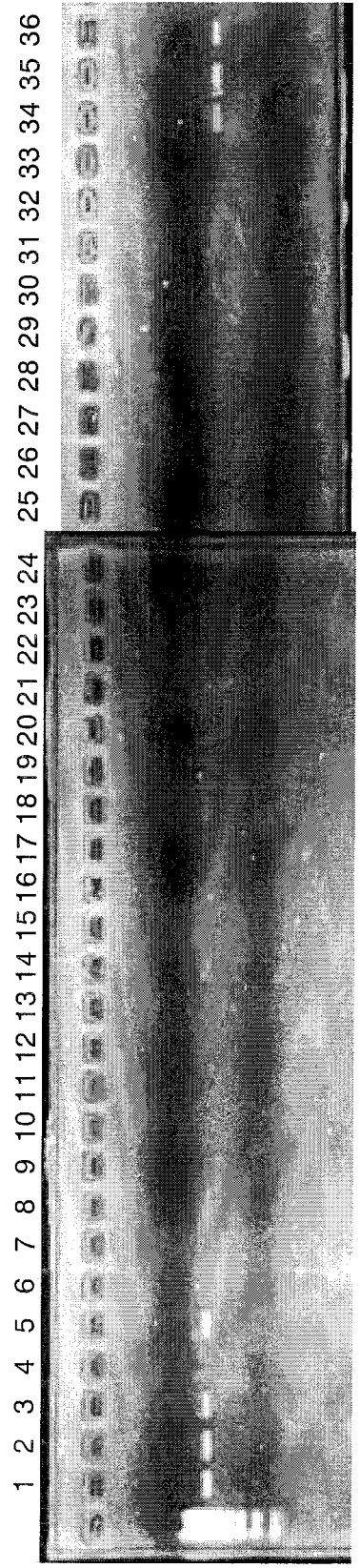
FIG. 2 shows a resultant band pattern from agarose gel electrophoresis of PCR-ed reaction solutions and ethidium bromide staining in the example 2. The number on each lane represents the number of the forward primer of Table 4 used for producing the PCR product on the gel.

The reaction solution was prepared overall in the same manner as that of the example 1 except for using the forward primers as of Table 4. The reaction solution was subjected to PCR through a treatment at 95° C. for 15 seconds, and subsequent 30 thermal cycles of 95° C. for 30 seconds and 68° C. for 6 minutes. Thereafter, 1 µL was each collected from the yielded reaction solution, then was subjected to agarose gel electrophoresis and ethidium bromide staining, by which a band pattern was obtained. FIG. 2 shows the resultant band pattern from the electrophoresis of the reaction solutions. The lane on the left is of an electrophoresed marker indicating the base pair lengths. Each lane number represents the number assigned to the forward primer of Table 4 used for producing the PCR product on the gel.

When 30 cycles were performed in the PCR with use of the primer having no nucleotide substitution, the PCR product was detected regardless of the presence or absence of the nucleotide insertion (see lanes 1 to 3). On the other hand, with use of the primer having a nucleotide substitution, the PCR amplification was found to be suppressed in many cases (see lanes 4 to 33). However, when the sixth nucleotide of the Fw_I02_P06 was substituted, the PCR product was detected irrespective of the type of the substituted nucleotide (see lanes 34 to 36). That is, with use of a primer in which one nucleotide was inserted on the 5' side of the fourth nucleotide from the 3' end, the PCR amplification was suppressed provided that the nucleotide at the position of the first to fourth nucleotide from the 3' end was substituted; while, with use of a primer in which two nucleotides were inserted on the 5' side of the sixth nucleotide from the 3' end, the PCR amplification was suppressed provided that the nucleotide at the position of the first to fifth nucleotide from the 3' end was substituted.

These results implies that: even if a long primer of 30 or more nucleotides is used, it is possible to identify a single nucleotide difference, by artificially inserting nucleotide(s) into the primer to destabilize the hybridization between the primer and the target nucleic acid at the terminal; and that the position of the analyte nucleotide(s) is not limited to the 3' end or the second nucleotide from the 3' end.

EXAMPLE 3

A comparison was made between the nucleic acid detection method of the present invention and conventional SNP detection methods by means of the SSP-PCR method or the ASP-PCR method. The SNP (A/G) having the NCBI accession number of rs4994 was used as the analyte SNP.

Primer Design

The primer A for identifying the A allele and the primer G for identifying the G allele were respectively designed according to a variety of methods. The respective sequences of the thus designed primers are shown in Table 5. Specifically speaking, in the SSP Primers A/G designed by the SSP-PCR method, the SNP-corresponding nucleotide was located at the 3' end. In the ASP Primers A/G designed by the ASP-PCR method, the SNP-corresponding nucleotide was located at the second nucleotide from the 3' end. In the ASP+ MM Primers A/G designed by the method of Patent Document 2 (mutation is introduced in the ASP-PCR method), the SNP-corresponding nucleotide was located at the second nucleotide from the 3' end, and one nucleotide at the third nucleotide from the 3' end was substituted. In the INS-SP Primers A/G designed by the nucleic acid detection method of the present invention, the SNP-corresponding nucleotide was located at the third nucleotide from the 3' end and two nucleotides were inserted on the 5' side of the fifth nucleotide from the 3' end. Furthermore, the INS-SPC Primers A/G were also designed as a control of the nucleic acid detection method of the present invention such that no nucleotide was inserted and the SNP-corresponding nucleotide was located at the third nucleotide from the 3' end.

TABLE 5

| Name | Seq |
|---|---|
| SSP PrimerA | ACGAACACGTTGGTCATGGTCTGGAGTCTCGGAGTCCA |
| SSP PrimerG | CGTTGGTCATGGTCTGGAGTCTCGGAGTCCG |
| ASP PrimerA | ACGAACACGTTGGTCATGGTCTGGAGTCTCGGAGTCCAG |
| ASP PrimerG | GAACACGTTGGTCATGGTCTGGAGTCTCGGAGTCCGG |
| ASP + MM PrimerA | GTCACGAACACGTTGGTCATGGTCTGGAGTCTCGGAGTCGAG |
| ASP + MM PrimerG | ACACGTTGGTCATGGTCTGGAGTCTCGGAGTCGGG |
| INS-SP PrimerA | ACGAACACGTTGGTCATGGTCTGGAGTCTCGGAGTAACCAGG |
| INS-SP PrimerG | CACGTTGGTCATGGTCTGGAGTCTCGGAGTAACCGGG |
| INS-SPC PrimerA | TCACGAACACGTTGGTCATGGTCTGGAGTCTCGGAGTCCAGG |
| INS-SPC PrimerG | ACACGTTGGTCATGGTCTGGAGTCTCGGAGTCCGGG |
| ra4994 Rv Primer | TTGGGAGACCCCCTCCTTCCTTCTTTCCCTA |

Nucleic Acid Extension Reaction and Detection of Extension Product

PCR was conducted with use of the thus designed respective primers as of Table 5, and their PCR products were detected. The rs4994 Rv Primer was used as the reverse primer in all cases. In addition, the genome sample (AG) already known to be a heterozygote, the genome sample (AA) already known to be a homozygote consisting of A alleles, and the genome sample (GG) already known to be a homozygote consisting of G alleles, when it comes to the SNP of rs4994, were respectively used as templates.

Specifically speaking, 5 μL of 2×QIAGEN Multiplex PCR Master Mix (manufactured by QIAGEN) was added with 5 ng of each genome sample, and the forward primer and the reverse primer respectively at the final concentrations of 500 nM, to thereby prepare 10 μL of a reaction solution. The reaction solution was subjected to PCR through a treatment at 95° C. for 15 seconds, and subsequent 40 thermal cycles of 95° C. for 30 seconds and 68° C. for 6 minutes. Thereafter, the amount of the PCR product in the yielded reaction solution was determined by the image analysis on the band pattern and numerical conversion thereof by the 2100 BIOANALYZER (manufactured by Agilent). The results of the calculated amounts of the PCR products are shown in FIG. 3A to FIG. 3E.

Figure 3A:
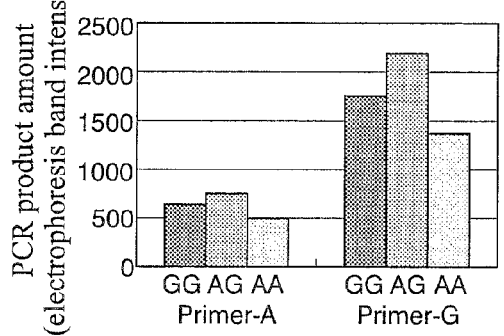
FIG. 3A is a graph showing the calculated results of the amounts of PCR products with use of SSP Primers A/G in the example 3.
Figure 3B:
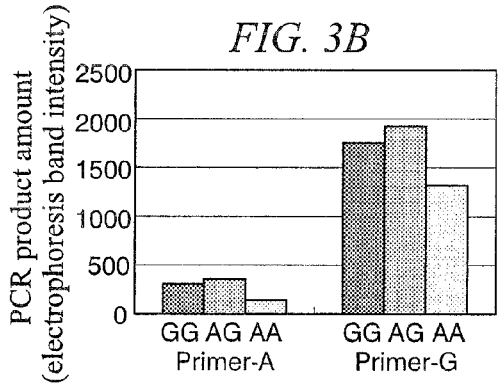
FIG. 3B is a graph showing the calculated results of the amounts of PCR products with use of ASP Primers A/G in the example 3.
Figure 3C:
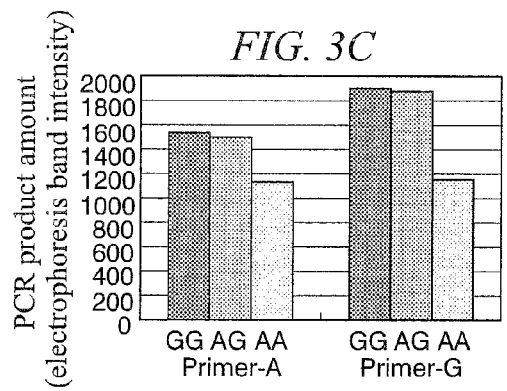
FIG. 3C is a graph showing the calculated results of the amounts of PCR products with use of ASP+MM Primers A/G in the example 3.
Figure 3D:
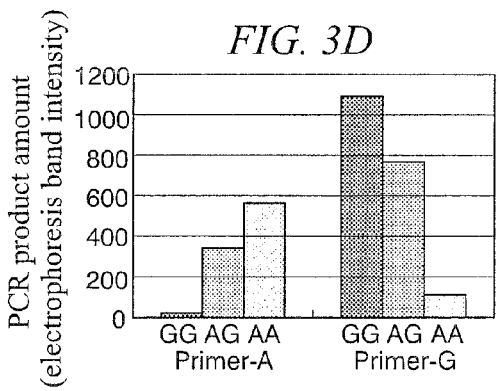
FIG. 3D is a graph showing the calculated results of the amounts of PCR products with use of INS-SP Primers A/G in the example 3.
Figure 3E:
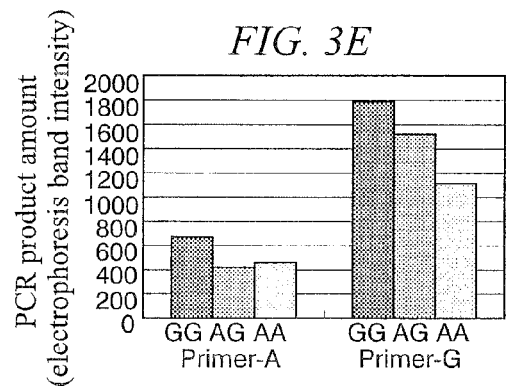
FIG. 3E is a graph showing the calculated results of the amounts of PCR products with use of INS-SPC Primers A/G in the example 3.

FIG. 3A shows the amounts of PCR products produced with use of the SSP Primers A/G, FIG. 3B shows the amounts of PCR products produced with use of the ASP Primers A/G, FIG. 3C shows the amounts of PCR products produced with use of the ASP+MM Primers A/G, FIG. 3D shows the amounts of PCR products produced with use of the INS-SP Primers A/G, and FIG. 3E shows the amounts of PCR products produced with use of the INS-SPC Primers A/G. In these graphs, the symbol GG shows the results of the genome sample (GG), the symbol AG shows the results of the genome sample (AG), and the symbol AA shows the results of the genome sample (AA). In results, the signals did not agree with the allele genotypes when using any one of the SSP Primers A/G, the ASP Primers A/G, and the ASP+MM Primers A/G. On the other hand, the signals agreed with the allele genotypes when using the INS-SP Primers A/G; whereas, no allele-specificity was detected when using the INS-SPC Primers A/G which had no insertion or deletion site. Accordingly, it was apparently possible by employing the nucleic acid detection method of the present invention to detect the SNP with the highest accuracy than ever before, in the case where a long primer is used.

EXAMPLE 4

The detection of the target nucleic acid was attempted by using analyte nucleotide-identification primers lacking some nucleotides as the insertion/deletion site. The SNP (A/G) having the NCBI accession number of rs4994 was used as the analyte SNP, likewise of the example 3.

Primer Design

The DEL-SP Primers A/G were designed so that the sixth and the seventh nucleotides from the 3' end were deleted from the INS-SPC Primers A/G of the example 3. The respective sequences of the thus designed primers are shown in Table 6.

TABLE 6

| Name | Seq |
|---|---|
| DEL-SP PrimerA | ACGAACACGTTGGTCATGGTCTGGAGTCTCGGAGTAACCAGG |
| DEL-SP PrimerG | CACGTTGGTCATGGTCTGGAGTCTCGGAGTAACCGGC |

Nucleic Acid Extension Reaction and Detection of Extension Product

Figure 4:
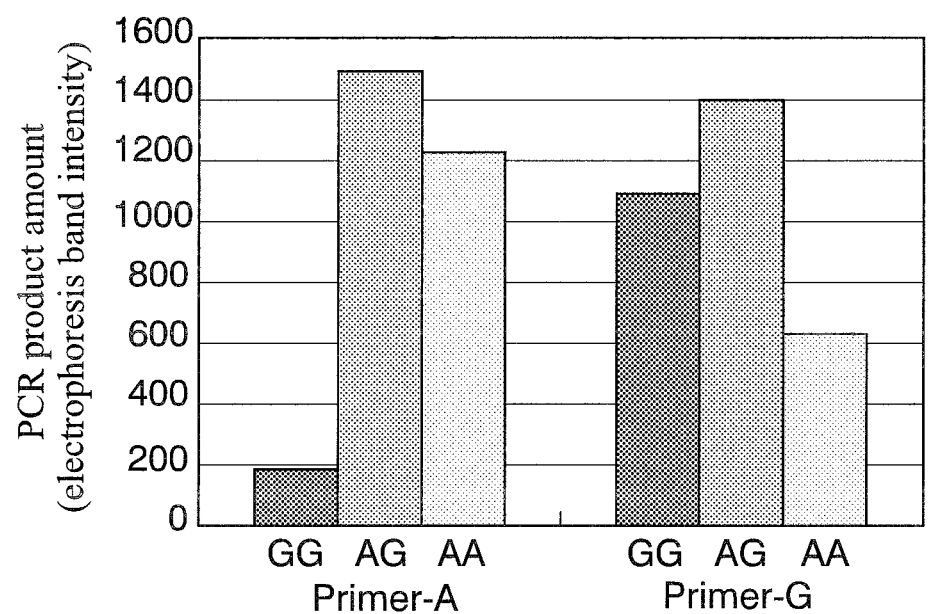
FIG. 4 is a graph showing the calculated results of the amounts of PCR products in the example 4.

PCR was performed in the same manner as that of the example 3 except for using the DEL-SP Primers A/G designed as of Table 6 as the forward primer. Then, the amounts of the PCR products in the yielded reaction solutions were measured. The results of the calculated amounts of the PCR products are shown in FIG. 4. In the graph, the symbol GG shows the results of the genome sample (GG), the symbol AG shows the results of the genome sample (AG), and the symbol AA shows the results of the genome sample (AA). In results, when using the DEL-SP Primers A/G, the allele genotype and the amount of the PCR product were correlated. From these results, even if nucleotide(s) was (were) deleted as the insertion or deletion site, it was apparently possible to produce a primer having high nucleotide identification ability similarly to the case where nucleotide(s) was (were) inserted.

INDUSTRIAL APPLICABILITY

The nucleic acid detection method of the present invention is capable of sufficiently accurate detection, no matter the nucleotide length of a primer, and no matter if the analyte nucleotide consists of only a single nucleotide. Therefore, the present invention can be applied to the field of genetic analysis, such as SNP analysis, in medical institutions of gene analyses where a large number of nucleic acid samples have to be handled for the detection of target nucleic acids, and such situations.

The invention claimed is:

1. A nucleic acid detection method comprising:
(a) performing a nucleic acid extension reaction by mixing:
a nucleic acid sample;
an analyte nucleotide-identification primer being a polynucleotide which comprises:
a nucleotide sequence being homologous or complementary to a partial region containing an analyte nucleotide on a target nucleotide sequence, and having an insertion site created by inserting one to three nucleotides or a deletion site created by deleting one to three nucleotides, wherein the insertion site and deletion site are on the 5' side of the nucleotide corresponding to the analyte nucleotide; and
a polymerase, wherein if the target nucleotide sequence that contains the analyte nucleotide is present in the mixture, an extension product is formed and if no analyte nucleotide is present in the mixture, no extension product is formed; and
(b) determining if the extension product is formed in the mixture of (a), which contains a nucleic acid having the target nucleotide sequence comprising one or more analyte nucleotide(s), thereby determining whether or not the extension product is created by the extension reaction.

2. The nucleic acid detection method according to claim 1, wherein said insertion site or said deletion site of said analyte nucleotide-identification primer is located on the 5' side of the third nucleotide from the 3' end of the primer.

3. The nucleic acid detection method according to claim 2, wherein said insertion site or said deletion site of said analyte nucleotide-identification primer is located on the 3' side of the twentieth nucleotide from the 3' end of the primer.

4. The nucleic acid detection method according to claim 1, wherein the method comprises, prior to (a),
(c) performing a nucleic acid extension reaction with use of: a nucleic acid in said nucleic acid sample; and an amplification primer being a polynucleotide which comprises a sequence complementary to said analyte nucleotide-identification primer, on the 5' end, and a nucleotide sequence homologous or complementary to a partial region of said target nucleotide sequence other than the partial region containing said analyte nucleotide(s), on the 3' end; so as to obtain a nucleic acid in which a nucleotide sequence homologous to the analyte nucleotide-identification primer is held on the 3' end of the target nucleotide sequence; and
in (a), a target nucleotide sequence-portion of the nucleic acid obtained in (c) is used as a template, and a 3' end-portion of the nucleic acid obtained in (c) as the analyte nucleotide-identification primer.

5. The nucleic acid detection method according to claim 1, wherein said insertion site is made by inserting one to three nucleotide(s).

6. The nucleic acid detection method according to claim 1, wherein said deletion site is made by deleting one to three nucleotide(s).

7. The nucleic acid detection method according to claim 1, wherein said nucleic acid extension reaction is a reaction to repeatedly perform a heat denaturation step, an annealing step, and an extension step.

8. The nucleic acid detection method according to claim 7, wherein the annealing temperature in said annealing step and the extension reaction temperature in said extension step are the same.

9. The nucleic acid detection method according to claim 1, wherein said analyte nucleotide-identification primer is a polynucleotide having a length of 30 or more nucleotides.

10. The nucleic acid detection method according to claim 1, wherein the annealing temperature for said analyte nucleotide-identification primer and the nucleic acid having said target nucleotide sequence is 68° C. or higher.

11. The nucleic acid detection method according to claim 7, wherein the sum of the annealing time in said annealing step and the extension reaction time is three or more minutes.

12. The nucleic acid detection method according to claim 7, wherein the annealing time in said annealing step is increased per each cycle.

13. The nucleic acid detection method according to claim 12, wherein the annealing time in the final cycle is three or more minutes.

14. The nucleic acid detection method according to claim 1, wherein said polymerase is an enzyme having a strand displacement activity, and said nucleic acid extension reaction is a reaction to repeatedly perform an annealing step and an extension step in a fixed temperature condition.

* * * * *

SEQUENCE LISTING

<160> NUMBER OF SEQ ID NOS: 68

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: Fw primer.

<400> SEQUENCE: 1
aggtgtcaga catacccctct ttttggagat ttcctgttcc                    40

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Re primer.

<400> SEQUENCE: 2
aattgctctg ctcttgtaag tctgggatgc tttcct                         36

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: Fw_I01_P01
      primer.

<400> SEQUENCE: 3
aggtgtcaga catacccctct ttttggagat ttcctgttct c                  41

<210> SEQ ID NO 4
<211> LENGTH: 41
<212> TYPE: DNA
<213> ORGANISM: Artificial Sequence
<220> FEATURE:
<223> OTHER INFORMATION: Description of Artificial Sequence: Fw_I01_P02
      primer.

<400> SEQUENCE: 4
aggtgtcaga catacccctct ttttggagat ttcctgttac c                  41

<210> SEQ ID NO 5
<211> LENGTH: 41
<212> TYPE: DNA
<213> ORGANISM: Artificial Sequence
<220> FEATURE:
<223> OTHER INFORMATION: Description of Artificial Sequence: Fw_I01_P03
      primer.

<400> SEQUENCE: 5
aggtgtcaga catacccctct ttttggagat ttcctgtatc c                  41

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Fw_I01_P04
      primer.

-continued

```
<400> SEQUENCE: 6
aggtgtcaga catacccuct ttttggagat ttcctgattc c                   41

<210> SEQ ID NO 7
<211> LENGTH: 41
<212> TYPE: DNA
<213> ORGANISM: Artificial Sequence
<220> FEATURE:
<223> OTHER INFORMATION: Description of Artificial Sequence: Fw_I01_P05
      primer.

<400> SEQUENCE: 7
aggtgtcaga catacccuct ttttggagat ttcctagttc c                   41

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: Fw_I01_P06
      primer.

<400> SEQUENCE: 8
aggtgtcaga catacccuct ttttggagat ttccatgttc c                   41

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: Fw_I01_P07
      primer.

<400> SEQUENCE: 9
aggtgtcaga catacccuct ttttggagat ttctctgttc c                   41

<210> SEQ ID NO 10
<211> LENGTH: 41
<212> TYPE: DNA
<213> ORGANISM: Artificial Sequence
<220> FEATURE:
<223> OTHER INFORMATION: Description of Artificial Sequence: Fw_I01_P08
      primer.

<400> SEQUENCE: 10
aggtgtcaga catacccuct ttttggagat ttacctgttc c                   41

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence: Fw_I02_P02
      primer.

<400> SEQUENCE: 11
aggtgtcaga catacccuct ttttggagat ttcctgttaa cc                  42

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: Fw_I02_P03
      primer.

<400> SEQUENCE: 12
```
aggtgtcaga cataccctct ttttggagat ttcctgtaat cc                              42

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence: Fw_I02_P04
      primer.

<400> SEQUENCE: 13
aggtgtcaga cataccctct ttttggagat ttcctgaatt cc                              42

<210> SEQ ID NO 14
<211> LENGTH: 42
<212> TYPE: DNA
<213> ORGANISM: Artificial Sequence
<220> FEATURE:
<223> OTHER INFORMATION: Description of Artificial Sequence: Fw_I02_P05
      primer.

<400> SEQUENCE: 14
aggtgtcaga cataccctct ttttggagat ttcctaagtt cc                              42

<210> SEQ ID NO 15
<211> LENGTH: 42
<212> TYPE: DNA
<213> ORGANISM: Artificial Sequence
<220> FEATURE:
<223> OTHER INFORMATION: Description of Artificial Sequence: Fw_I02_P06
      primer.

<400> SEQUENCE: 15
aggtgtcaga cataccctct ttttggagat ttccaatgtt cc                              42

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: Fw_I02_P07
      primer.

<400> SEQUENCE: 16
aggtgtcaga cataccctct ttttggagat ttcttctgtt cc                              42

<210> SEQ ID NO 17
<211> LENGTH: 43
<212> TYPE: DNA
<213> ORGANISM: Artificial Sequence
<220> FEATURE:
<223> OTHER INFORMATION: Description of Artificial Sequence: Fw_I03_P03
      primer.

<400> SEQUENCE: 17
aggtgtcaga cataccctct ttttggagat ttcctgtaaa tcc                             43

<210> SEQ ID NO 18
<211> LENGTH: 43
<212> TYPE: DNA
<213> ORGANISM: Artificial Sequence
<220> FEATURE:
<223> OTHER INFORMATION: Description of Artificial Sequence: Fw_I03_P04
      primer.

<400> SEQUENCE: 18
aggtgtcaga cataccctct ttttggagat ttcctgaaat tcc                             43

```
<210> SEQ ID NO 19
<211> LENGTH: 43
<212> TYPE: DNA
<213> ORGANISM: Artificial Sequence
<220> FEATURE:
<223> OTHER INFORMATION: Description of Artificial Sequence: Fw_I03_P05
      primer.

<400> SEQUENCE: 19
aggtgtcaga cataccctct ttttggagat ttcctaaagt tcc                         43

<210> SEQ ID NO 20
<211> LENGTH: 43
<212> TYPE: DNA
<213> ORGANISM: Artificial Sequence
<220> FEATURE:
<223> OTHER INFORMATION: Description of Artificial Sequence: Fw_I03_P06
      primer.

<400> SEQUENCE: 20
aggtgtcaga cataccctct ttttggagat ttccaaatgt tcc                         43

<210> SEQ ID NO 21
<211> LENGTH: 43
<212> TYPE: DNA
<213> ORGANISM: Artificial Sequence
<220> FEATURE:
<223> OTHER INFORMATION: Description of Artificial Sequence: Fw_I03_P07
      primer.

<400> SEQUENCE: 21
aggtgtcaga cataccctct ttttggagat ttctttctgt tcc                         43

<210> SEQ ID NO 22
<211> LENGTH: 43
<212> TYPE: DNA
<213> ORGANISM: Artificial Sequence
<220> FEATURE:
<223> OTHER INFORMATION: Description of Artificial Sequence: Fw_I03_P08
      primer.

<400> SEQUENCE: 22
aggtgtcaga cataccctct ttttggagat ttaaacctgt tcc                         43

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Fw_1A
      primer.

<400> SEQUENCE: 23
aggtgtcaga cataccctct ttttggagat ttcctgttca                             40

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Fw_1T
      primer.

<400> SEQUENCE: 24
aggtgtcaga cataccctct ttttggagat ttcctgttct                             40
```

```
<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Fw_1G
      primer.

<400> SEQUENCE: 25
aggtgtcaga catccctct ttttggagat ttcctgttcg                    40

<210> SEQ ID NO 26
<211> LENGTH: 41
<212> TYPE: DNA
<213> ORGANISM: Artificial Sequence
<220> FEATURE:
<223> OTHER INFORMATION: Description of Artificial Sequence:
      Fw_I01_P04_1A primer.

<400> SEQUENCE: 26
aggtgtcaga catccctct ttttggagat ttcctgattc a                  41

<210> SEQ ID NO 27
<211> LENGTH: 41
<212> TYPE: DNA
<213> ORGANISM: Artificial Sequence
<220> FEATURE:
<223> OTHER INFORMATION: Description of Artificial Sequence:
      Fw_I01_P04_1T primer.

<400> SEQUENCE: 27
aggtgtcaga catccctct ttttggagat ttcctgattc t                  41

<210> SEQ ID NO 28
<211> LENGTH: 41
<212> TYPE: DNA
<213> ORGANISM: Artificial Sequence
<220> FEATURE:
<223> OTHER INFORMATION: Description of Artificial Sequence:
      Fw_I01_P04_1G primer.

<400> SEQUENCE: 28
aggtgtcaga catccctct ttttggagat ttcctgattc g                  41

<210> SEQ ID NO 29
<211> LENGTH: 41
<212> TYPE: DNA
<213> ORGANISM: Artificial Sequence
<220> FEATURE:
<223> OTHER INFORMATION: Description of Artificial Sequence:
      Fw_I01_P04_2A primer.

<400> SEQUENCE: 29
aggtgtcaga catccctct ttttggagat ttcctgatta c                  41

<210> SEQ ID NO 30
<211> LENGTH: 41
<212> TYPE: DNA
<213> ORGANISM: Artificial Sequence
<220> FEATURE:
<223> OTHER INFORMATION: Description of Artificial Sequence:
      Fw_I01_P04_2T primer.

<400> SEQUENCE: 30
aggtgtcaga catccctct ttttggagat ttcctgattt c                  41

<210> SEQ ID NO 31
<211> LENGTH: 41
```

```
<212> TYPE: DNA
<213> ORGANISM: Artificial Sequence
<220> FEATURE:
<223> OTHER INFORMATION: Description of Artificial Sequence:
      Fw_I01_P04_2G primer.

<400> SEQUENCE: 31
aggtgtcaga catacccctct ttttggagat ttcctgattg c            41

<210> SEQ ID NO 32
<211> LENGTH: 41
<212> TYPE: DNA
<213> ORGANISM: Artificial Sequence
<220> FEATURE:
<223> OTHER INFORMATION: Description of Artificial Sequence:
      Fw_I01_P04_3A primer.

<400> SEQUENCE: 32
aggtgtcaga catacccctct ttttggagat ttcctgatac c            41

<210> SEQ ID NO 33
<211> LENGTH: 41
<212> TYPE: DNA
<213> ORGANISM: Artificial Sequence
<220> FEATURE:
<223> OTHER INFORMATION: Description of Artificial Sequence:
      Fw_I01_P04_3C primer.

<400> SEQUENCE: 33
aggtgtcaga catacccctct ttttggagat ttcctgatcc c            41

<210> SEQ ID NO 34
<211> LENGTH: 41
<212> TYPE: DNA
<213> ORGANISM: Artificial Sequence
<220> FEATURE:
<223> OTHER INFORMATION: Description of Artificial Sequence:
      Fw_I01_P04_3G primer.

<400> SEQUENCE: 34
aggtgtcaga catacccctct ttttggagat ttcctgatgc c            41

<210> SEQ ID NO 35
<211> LENGTH: 41
<212> TYPE: DNA
<213> ORGANISM: Artificial Sequence
<220> FEATURE:
<223> OTHER INFORMATION: Description of Artificial Sequence:
      Fw_I01_P04_4A primer.

<400> SEQUENCE: 35
aggtgtcaga catacccctct ttttggagat ttcctgaatc c            41

<210> SEQ ID NO 36
<211> LENGTH: 41
<212> TYPE: DNA
<213> ORGANISM: Artificial Sequence
<220> FEATURE:
<223> OTHER INFORMATION: Description of Artificial Sequence:
      Fw_I01_P04_4C primer.

<400> SEQUENCE: 36
aggtgtcaga catacccctct ttttggagat ttcctgactc c            41

<210> SEQ ID NO 37
<211> LENGTH: 41
<212> TYPE: DNA
<213> ORGANISM: Artificial Sequence
```

-continued

```
<220> FEATURE:
<223> OTHER INFORMATION: Description of Artificial Sequence:
      Fw_I01_P04_4G primer.

<400> SEQUENCE: 37
aggtgtcaga cataccctct ttttggagat ttcctgagtc c                          41

<210> SEQ ID NO 38
<211> LENGTH: 42
<212> TYPE: DNA
<213> ORGANISM: Artificial Sequence
<220> FEATURE:
<223> OTHER INFORMATION: Description of Artificial Sequence:
      Fw_I02_P06_1A primer.

<400> SEQUENCE: 38
aggtgtcaga cataccctct ttttggagat ttccaatgtt ca                         42

<210> SEQ ID NO 39
<211> LENGTH: 42
<212> TYPE: DNA
<213> ORGANISM: Artificial Sequence
<220> FEATURE:
<223> OTHER INFORMATION: Description of Artificial Sequence:
      Fw_I02_P06_1T primer.

<400> SEQUENCE: 39
aggtgtcaga cataccctct ttttggagat ttccaatgtt ct                         42

<210> SEQ ID NO 40
<211> LENGTH: 42
<212> TYPE: DNA
<213> ORGANISM: Artificial Sequence
<220> FEATURE:
<223> OTHER INFORMATION: Description of Artificial Sequence:
      Fw_I02_P06_1G primer.

<400> SEQUENCE: 40
aggtgtcaga cataccctct ttttggagat ttccaatgtt cg                         42

<210> SEQ ID NO 41
<211> LENGTH: 42
<212> TYPE: DNA
<213> ORGANISM: Artificial Sequence
<220> FEATURE:
<223> OTHER INFORMATION: Description of Artificial Sequence:
      Fw_I02_P06_2A primer.

<400> SEQUENCE: 41
aggtgtcaga cataccctct ttttggagat ttccaatgtt ac                         42

<210> SEQ ID NO 42
<211> LENGTH: 42
<212> TYPE: DNA
<213> ORGANISM: Artificial Sequence
<220> FEATURE:
<223> OTHER INFORMATION: Description of Artificial Sequence:
      Fw_I02_P06_2T primer.

<400> SEQUENCE: 42
aggtgtcaga cataccctct ttttggagat ttccaatgtt tc                         42

<210> SEQ ID NO 43
<211> LENGTH: 42
<212> TYPE: DNA
<213> ORGANISM: Artificial Sequence
<220> FEATURE:
<223> OTHER INFORMATION: Description of Artificial Sequence:
```

-continued

Fw_I02_P06_2G primer.

<400> SEQUENCE: 43
aggtgtcaga catacccctct ttttggagat ttccaatgtt gc        42

<210> SEQ ID NO 44
<211> LENGTH: 42
<212> TYPE: DNA
<213> ORGANISM: Artificial Sequence
<220> FEATURE:
<223> OTHER INFORMATION: Description of Artificial Sequence:
      Fw_I02_P06_3A primer.

<400> SEQUENCE: 44
aggtgtcaga catacccctct ttttggagat ttccaatgta gc        42

<210> SEQ ID NO 45
<211> LENGTH: 42
<212> TYPE: DNA
<213> ORGANISM: Artificial Sequence
<220> FEATURE:
<223> OTHER INFORMATION: Description of Artificial Sequence:
      Fw_I02_P06_3C primer.

<400> SEQUENCE: 45
aggtgtcaga catacccctct ttttggagat ttccaatgtc cc        42

<210> SEQ ID NO 46
<211> LENGTH: 42
<212> TYPE: DNA
<213> ORGANISM: Artificial Sequence
<220> FEATURE:
<223> OTHER INFORMATION: Description of Artificial Sequence:
      Fw_I02_P06_3G primer.

<400> SEQUENCE: 46
aggtgtcaga catacccctct ttttggagat ttccaatgtg cc        42

<210> SEQ ID NO 47
<211> LENGTH: 42
<212> TYPE: DNA
<213> ORGANISM: Artificial Sequence
<220> FEATURE:
<223> OTHER INFORMATION: Description of Artificial Sequence:
      Fw_I02_P06_4A primer.

<400> SEQUENCE: 47
aggtgtcaga catacccctct ttttggagat ttccaatgat cc        42

<210> SEQ ID NO 48
<211> LENGTH: 42
<212> TYPE: DNA
<213> ORGANISM: Artificial Sequence
<220> FEATURE:
<223> OTHER INFORMATION: Description of Artificial Sequence:
      Fw_I02_P06_4C primer.

<400> SEQUENCE: 48
aggtgtcaga catacccctct ttttggagat ttccaatgct cc        42

<210> SEQ ID NO 49
<211> LENGTH: 42
<212> TYPE: DNA
<213> ORGANISM: Artificial Sequence
<220> FEATURE:
<223> OTHER INFORMATION: Description of Artificial Sequence:
      Fw_I02_P06_4G primer.

```
<400> SEQUENCE: 49
aggtgtcaga catacccctct ttttggagat tccaatggt cc                    42

<210> SEQ ID NO 50
<211> LENGTH: 42
<212> TYPE: DNA
<213> ORGANISM: Artificial Sequence
<220> FEATURE:
<223> OTHER INFORMATION: Description of Artificial Sequence:
      Fw_I02_P06_5A primer.

<400> SEQUENCE: 50
aggtgtcaga catacccctct ttttggagat tccaatatt cc                    42

<210> SEQ ID NO 51
<211> LENGTH: 42
<212> TYPE: DNA
<213> ORGANISM: Artificial Sequence
<220> FEATURE:
<223> OTHER INFORMATION: Description of Artificial Sequence:
      Fw_I02_P06_5T primer.

<400> SEQUENCE: 51
aggtgtcaga catacccctct ttttggagat tccaatttt cc                    42

<210> SEQ ID NO 52
<211> LENGTH: 42
<212> TYPE: DNA
<213> ORGANISM: Artificial Sequence
<220> FEATURE:
<223> OTHER INFORMATION: Description of Artificial Sequence:
      Fw_I02_P06_5C primer.

<400> SEQUENCE: 52
aggtgtcaga catacccctct ttttggagat tccaatctt cc                    42

<210> SEQ ID NO 53
<211> LENGTH: 42
<212> TYPE: DNA
<213> ORGANISM: Artificial Sequence
<220> FEATURE:
<223> OTHER INFORMATION: Description of Artificial Sequence:
      Fw_I02_P06_6A primer.

<400> SEQUENCE: 53
aggtgtcaga catacccctct ttttggagat tccaaagtt cc                    42

<210> SEQ ID NO 54
<211> LENGTH: 42
<212> TYPE: DNA
<213> ORGANISM: Artificial Sequence
<220> FEATURE:
<223> OTHER INFORMATION: Description of Artificial Sequence:
      Fw_I02_P06_6C primer.

<400> SEQUENCE: 54
aggtgtcaga catacccctct ttttggagat tccaacgtt cc                    42

<210> SEQ ID NO 55
<211> LENGTH: 42
<212> TYPE: DNA
<213> ORGANISM: Artificial Sequence
<220> FEATURE:
<223> OTHER INFORMATION: Description of Artificial Sequence:
      Fw_I02_P06_6G primer.

<400> SEQUENCE: 55
```
aggtgtcaga catacccctct ttttggagat ttccaaggtt cc    42

<210> SEQ ID NO 56
<211> LENGTH: 38
<212> TYPE: DNA
<213> ORGANISM: Artificial Sequence
<220> FEATURE:
<223> OTHER INFORMATION: Description of Artificial Sequence: SSP
      PrimerA.

<400> SEQUENCE: 56
acgaacacgt tggtcatggt ctggagtctc ggagtcca    38

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: SSP
      PrimerG.

<400> SEQUENCE: 57
cgttggtcat ggtctggagt ctcggagtcc g    31

<210> SEQ ID NO 58
<211> LENGTH: 39
<212> TYPE: DNA
<213> ORGANISM: Artificial Sequence
<220> FEATURE:
<223> OTHER INFORMATION: Description of Artificial Sequence: ASP
      PrimerA.

<400> SEQUENCE: 58
acgaacacgt tggtcatggt ctggagtctc ggagtccag    39

<210> SEQ ID NO 59
<211> LENGTH: 37
<212> TYPE: DNA
<213> ORGANISM: Artificial Sequence
<220> FEATURE:
<223> OTHER INFORMATION: Description of Artificial Sequence: ASP
      PrimerG.

<400> SEQUENCE: 59
gaacacgttg gtcatggtct ggagtctcgg agtccgg    37

<210> SEQ ID NO 60
<211> LENGTH: 42
<212> TYPE: DNA
<213> ORGANISM: Artificial Sequence
<220> FEATURE:
<223> OTHER INFORMATION: Description of Artificial Sequence: ASP+MM
      PrimerA.

<400> SEQUENCE: 60
gtcacgaaca cgttggtcat ggtctggagt ctcggagtcg ag    42

<210> SEQ ID NO 61
<211> LENGTH: 35
<212> TYPE: DNA
<213> ORGANISM: Artificial Sequence
<220> FEATURE:
<223> OTHER INFORMATION: Description of Artificial Sequence: ASP+MM
      PrimerG.

<400> SEQUENCE: 61
acacgttggt catggtctgg agtctcggag tcggg    35

```
<210> SEQ ID NO 62
<211> LENGTH: 42
<212> TYPE: DNA
<213> ORGANISM: Artificial Sequence
<220> FEATURE:
<223> OTHER INFORMATION: Description of Artificial Sequence: INS-SP
      PrimerA.

<400> SEQUENCE: 62
acgaacacgt tggtcatggt ctggagtctc ggagtaacca gg                          42

<210> SEQ ID NO 63
<211> LENGTH: 37
<212> TYPE: DNA
<213> ORGANISM: Artificial Sequence
<220> FEATURE:
<223> OTHER INFORMATION: Description of Artificial Sequence: INS-SP
      PrimerG.

<400> SEQUENCE: 63
cacgttggtc atggtctgga gtctcggagt aaccggg                                37

<210> SEQ ID NO 64
<211> LENGTH: 42
<212> TYPE: DNA
<213> ORGANISM: Artificial Sequence
<220> FEATURE:
<223> OTHER INFORMATION: Description of Artificial Sequence: INS-SPC
      PrimerA.

<400> SEQUENCE: 64
tcacgaacac gttggtcatg gtctggagtc tcggagtcca gg                          42

<210> SEQ ID NO 65
<211> LENGTH: 36
<212> TYPE: DNA
<213> ORGANISM: Artificial Sequence
<220> FEATURE:
<223> OTHER INFORMATION: Description of Artificial Sequence: INS-SPC
      PrimerG.

<400> SEQUENCE: 65
acacgttggt catggtctgg agtctcggag tccggg                                 36

<210> SEQ ID NO 66
<211> LENGTH: 31
<212> TYPE: DNA
<213> ORGANISM: Artificial Sequence
<220> FEATURE:
<223> OTHER INFORMATION: Description of Artificial Sequence: rs4994 Rv
      Primer.

<400> SEQUENCE: 66
ttgggagacc ccctccttcc ttctttccct a                                      31

<210> SEQ ID NO 67
<211> LENGTH: 42
<212> TYPE: DNA
<213> ORGANISM: Artificial Sequence
<220> FEATURE:
<223> OTHER INFORMATION: Description of Artificial Sequence: DEL-SP
      PrimerA.

<400> SEQUENCE: 67
acgaacacgt tggtcatggt ctggagtctc ggagtaacca gg                          42

<210> SEQ ID NO 68
```

```
<211> LENGTH: 37
<212> TYPE: DNA
<213> ORGANISM: Artificial Sequence
<220> FEATURE:
<223> OTHER INFORMATION: Description of Artificial Sequence: DEL-SP
      PrimerG.

<400> SEQUENCE: 68
cacgttggtc atggtctgga gtctcggagt aaccggg                           37
```